(12) United States Patent
Westerhof et al.

(10) Patent No.: US 11,553,873 B2
(45) Date of Patent: Jan. 17, 2023

(54) DEVICE AND METHOD FOR MEASURING SKIN ELASTICITY

(71) Applicant: KONINKLIJKE PHILIPS N.V., Eindhoven (NL)

(72) Inventors: Willem Auke Westerhof, Drachten (NL); Matthijs Paltje, Groningen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 927 days.

(21) Appl. No.: 16/323,809

(22) PCT Filed: Aug. 9, 2017

(86) PCT No.: PCT/EP2017/070259
§ 371 (c)(1),
(2) Date: Feb. 7, 2019

(87) PCT Pub. No.: WO2018/029286
PCT Pub. Date: Feb. 15, 2018

(65) Prior Publication Data
US 2019/0209074 A1    Jul. 11, 2019

(30) Foreign Application Priority Data
Aug. 9, 2016   (EP) .................................... 16183306

(51) Int. Cl.
*A61B 5/00* (2006.01)

(52) U.S. Cl.
CPC ............ *A61B 5/442* (2013.01); *A61B 5/0053* (2013.01); *A61B 5/0077* (2013.01); *A61B 5/0079* (2013.01)

(58) Field of Classification Search
None
See application file for complete search history.

(56) References Cited

U.S. PATENT DOCUMENTS

| | | | |
|---|---|---|---|
| 2003/0026110 A1* | 2/2003 | Satoh | H04N 5/2256 362/572 |
| 2006/0239547 A1* | 10/2006 | Robinson | G06T 7/0012 382/162 |
| 2012/0172685 A1 | 7/2012 | Gilbert | |
| 2012/0215134 A1 | 8/2012 | Hunter-Jones | |
| 2012/0253224 A1 | 10/2012 | Mir | |
| 2013/0079643 A1* | 3/2013 | Korichi | A61B 5/442 600/474 |
| 2013/0300919 A1* | 11/2013 | Fletcher | H04N 5/2254 348/360 |

(Continued)

FOREIGN PATENT DOCUMENTS

| | | |
|---|---|---|
| EP | 2687151 A1 | 1/2014 |
| JP | S62164438 A | 7/1987 |

(Continued)

*Primary Examiner* — Amelie R Davis
*Assistant Examiner* — Marjan Saboktakin

(57) ABSTRACT

Presented is a device (100), comprising: a means for attaching the device to an image recording device; a mechanical means configured for applying a pre-defined pressure to skin such that skin is deformed under the pre-defined pressure; and wherein the mechanical means is adapted such that an image of the deformed skin can be recorded by the image recording device when the device is attached to the image recording device. Further, a system and a method for determining skin elasticity is presented.

19 Claims, 4 Drawing Sheets

(56) References Cited

U.S. PATENT DOCUMENTS

| | | |
|---|---|---|
| 2015/0173996 A1 | 6/2015 | Grez |
| 2016/0183804 A1 | 6/2016 | Kowalewski |
| 2021/0052212 A1* | 2/2021 | Yaroslavsky ........ A61B 5/4836 |

FOREIGN PATENT DOCUMENTS

| | | | |
|---|---|---|---|
| JP | 2008029578 A | | 2/2008 |
| KR | 20060114881 A | * | 11/2006 |
| KR | 20060114881 A | | 11/2006 |
| RU | 2422081 C2 | | 6/2011 |
| WO | 2009027898 A1 | | 3/2009 |
| WO | 2010118124 A2 | | 10/2010 |
| WO | 2014029509 A1 | | 2/2014 |

* cited by examiner

DEVICE AND METHOD FOR MEASURING SKIN ELASTICITY

This application is the U.S. National Phase application under 35 U.S.C. § 371 of International Application No. PCT/EP2017/070259, filed on Aug. 9, 2017, which claims the benefit of International Application No. 16183306.6 filed on Aug. 9, 2016. These applications are hereby incorporated by reference herein.

FIELD OF THE INVENTION

The present invention relates to methods and devices for measuring skin properties. In particular, the invention relates to methods and devices for measuring skin elasticity.

BACKGROUND OF THE INVENTION

Skin is the largest organ of the human body and reflects a person's health and appearance. It has properties which are influenced by many factors. One of those properties is skin elasticity. Information on skin elasticity can be used to guide a person's skin care routine, personalized to his or her specific skin needs. Devices for validly measuring skin elasticity are expensive and are not available to most consumers.

State of the art skin elasticity measurement devices make use of a suction or indentation body to deform the skin. The displacement of the skin in reaction to the applied suction or indentation is measured and skin elasticity is determined based on the measured displacement. Because of their size and cost, these devices are intended for the professional market and are therefore not available to consumers at home.

US2012/0253224 describes an apparatus and method for making an apparatus for skin testing includes a housing with an opening which defines a field of view of a skin testing region, an image sensing apparatus, an illumination apparatus, a binding apparatus, and an image processing controller. The image sensing apparatus is positioned with respect to the housing to capture images in the field of view provided by the opening. The illumination apparatus is positioned within the housing to direct light towards a portion of the field of view provided by the opening. The binding apparatus detachably secures the housing over the skin testing region and maintains a fixed distance between the image sensing apparatus and the skin testing region. The controller is configured to analyze test samples sites in each of the captured images from the image sensing apparatus and provide a skin test result for each of the test sample sites.

US2013/0079643 describes a method of measuring the elasticity and firmness of skin. The invention also relates to methods of measuring improvements in a person's skin health by measuring firmness and elasticity before, during and after a cosmetic treatment. The invention further relates to methods of measuring the improvement in a person's skin firmness and elasticity that a cosmetic agent may cause when applied on the skin.

WO2014/029509 describes a device for determining elastic and/or visco-elastic properties of skin or scalp, comprising a measuring probe having a probe pin and a measurement system for registering a displacement of the probe pin, wherein the probe pin is provided in a probe chamber having an opening for contact of the probe pin with skin or scalp, the probe pin being biased to be flush with the opening or to protrude from the opening, a surrounding of the opening and/or a part of the opening being provided with one or more recesses, the device further comprising a pump connected to each of the recesses for applying an under-pressure in each of the one or more recesses.

EP2687151 describes a viscoelasticity measuring apparatus that measures viscoelasticity of a measurement target with high precision is provided. The measuring apparatus includes: a casing; a surface contact part provided in the casing and brought into surface contact with skin; a ball indenter that moves toward the skin more than the surface contact part and is pushed into the skin; a driving unit that supports the ball indenter and moves the ball indenter toward the skin; a load cell whose right end side is fixed to the casing and left end side supports the driving unit, the load cell detecting a pushing load that pushes the ball indenter into the skin; and a control unit that obtains displacement of the ball indenter.

There is a need for an inexpensive, reliable device for measuring skin elasticity at home.

SUMMARY OF THE INVENTION

In a first aspect of the invention a device for measuring skin elasticity is presented. The device may comprise a means for attaching the device to an image recording device. The device further comprises a mechanical means configured such that skin deforms under influence of a pre-defined pressure when the mechanical means is pressed against the skin. The pre-defined pressure may be provided by a mechanical device that stores energy and that is present in the mechanical means, e.g. a spring. The mechanical means is adapted or shaped such that an image of the deformed skin can be recorded by the image recording device when the device is attached to an image recording device. Thus, when the device is attached to the image recording device and when the mechanical means is deforming the skin, an image of the deformed skin can be recorded. Specific embodiments are described below and in the accompanying claims.

According to an embodiment of the invention, the mechanical means comprises an outer structure and an inner structure which is partly located inside the outer structure. A part of the inner structure is located outside of the outer structure when the device is not in use. The inner structure is moveable inside the outer structure. The inner structure can move completely inside the outer structure. A spring is present for providing the pre-defined pressure. The spring is coupled to the inner structure and positioned such that it compresses when the inner structure moves inside the outer structure. The inner structure is configured to cause the skin to deform when the device is pressed against the skin and when the inner structure moves inside the outer structure. For example, the inner structure may comprise two elements that causes skin deformation, e.g. doming, when pressed against the skin. For example, the end of the inner structure that touches the skin when the device is pressed against the skin may feature an opening which allows the skin to protrude the opening. The opening may be circular, e.g. for causing skin doming.

According to an embodiment of the invention, the device further comprises a first mirror positioned inside the inner structure. According to an embodiment of the invention, the first mirror is positioned such that an image taken by the image recording device contains a view of the skin deformation under an angle, e.g. 45 degrees relative to the skin plane. The first mirror may be attached to the inner structure. The mirror allows the recording of images of the skin deformation parallel to the skin plane. This way, a silhouette image of the skin deformation can be observed by the camera of the image recording device. From this image, skin elasticity can be determined. According to an embodiment of the invention, the mirror is placed at an angle between 45 and 75 degrees relative to the skin plane.

According to an embodiment of the invention, the device is adapted such that when it is attached to an image recording device, the image recording device can take an image which contains a direct view of the skin deformation and a view of the skin deformation obtained via the first mirror. Thus, in such an embodiment the image contains two parts. Both parts of the image may be used to determine skin elasticity. It is an advantage of the invention that by using information from different views, a more accurate determination of the skin elasticity can be obtained. For example, from both parts of the image, 3D information can be extracted which may be used to determine skin elasticity more accurately.

According to an embodiment of the invention, the device further comprises a second mirror. The first mirror is positioned inside the device for reflecting light towards the skin deformation from one direction. It is an advantage of the invention that by providing illumination to the skin deformation from two sides, shadows in the mirrors are created which simplify the image analysis of the skin deformation, e.g. a skin dome. The second mirror is positioned inside the device for reflecting light towards the skin deformation from another direction.

According to an embodiment of the invention, deformation of the skin is achieved without the use of pumps or other suction devices. It is an advantage of the invention that expensive components such as pumps are not required thereby reducing cost of the device.

According to an embodiment of the invention, the inner structure comprises two elements configured to move towards each other when the device is pressed against the skin and when the inner structure moves inside the outer structure thereby causing the skin in between the two elements to fold.

According to an embodiment of the invention, the inner structure comprises two elements configured to cause doming of skin present between the two elements when the device is pressed against the skin and when the inner structure moves inside the outer structure.

In yet a further aspect, the invention also provides a device including such image recording device or functionally coupled to such image recording device. Such functional combination is herein also indicated as "system". Hence, in embodiments the invention provides a system for determining the skin elasticity. The system comprises a image recording devices as well as the device, wherein the device is functionally coupled to the image recording device, such as attached (with means for attaching). The device itself (further) comprises, as indicated above, a mechanical means configured for applying a pre-defined pressure to skin such that skin is deformed under the pre-defined pressure. The mechanical means is adapted such that an image of the deformed skin can be recorded by the image recording device when the device is attached to the image recording device. Such system especially comprises a processor that is configured for determining an amount of deformation of the skin in the image using image processing techniques. The processor is further configured for determining skin elasticity based on the amount of skin deformation and on the pre-defined pressure value. Further, such image recording device especially comprises an imager for imaging the skin deformation and a light source for illuminating the skin deformation. Specific embodiments are described below and in the accompanying claims.

In an aspect of the invention, a system for determining skin elasticity is presented, comprising: a mechanical means for exposing skin to a pre-defined pressure when applied to or pressed against skin thereby creating a skin deformation such as a skin dome or skin folds. The system further comprises an image recording device comprising an imager for imaging the skin deformation and a light source for illuminating the skin deformation. The system further comprises a processor that is configured for determining an amount of deformation of the skin in the image using image processing techniques. The processor is further configured for determining skin elasticity based on the amount of skin deformation and on the pre-defined pressure value. Specific embodiments are described below and in the accompanying claims.

According to an embodiment of the invention, determining an amount of deformation of the skin comprises determining amplitude of skin folds in the deformed skin area and/or determining an amount of skin folds in the deformed skin area.

According to an embodiment of the invention, determining an amount of the skin deformation comprises analyzing light intensity differences in the image.

In a third aspect of the invention, a method for determining skin elasticity of skin is presented. The method comprises: receiving an image of deformed skin; receiving a pressure value to which the skin was exposed to create the deformed skin; determining an amount of deformation of the skin in the image using image processing techniques; determining skin elasticity of the skin based on the amount of skin deformation and on the pressure value. The method may be applied with the device as described herein and/or the system as described herein. Hence, in embodiments the method uses (or applies) the device or system. In specific embodiments, the method may further comprise using the device attached with means for attaching the device to an image recording device, wherein the image recording device comprises a smartphone. Specific embodiments are described below and in the accompanying claims.

According to an embodiment of the invention, determining the amount of deformation of the skin comprises determining amplitude and/or determining an amount of skin folds in the deformed skin area.

According to an embodiment of the invention, determining the amount of the skin deformation comprises analyzing light intensity differences in the image.

According to an embodiment of the invention, analyzing light intensity differences comprises: setting a light intensity threshold; calculating an area of the image having a light intensity larger than the threshold; and determining the amount of skin deformation based on the calculated area. The setting of the light intensity threshold may be based on averages, e.g. abs value per pixel in an area of the image.

According to an embodiment of the invention, analyzing light intensity differences comprises: setting or selecting a first light intensity threshold; calculating a first area of the image having a light intensity higher than the first threshold; setting or selecting a second light intensity threshold being lower than the first threshold; calculating a second area of the image having a light intensity lower than the second threshold; and determining the amount of skin deformation using the calculated first and second area. It is an advantage of the invention that by using multiple light thresholds, the amount of skin deformation can be determined more accurately leading to a more accurate skin elasticity determination.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
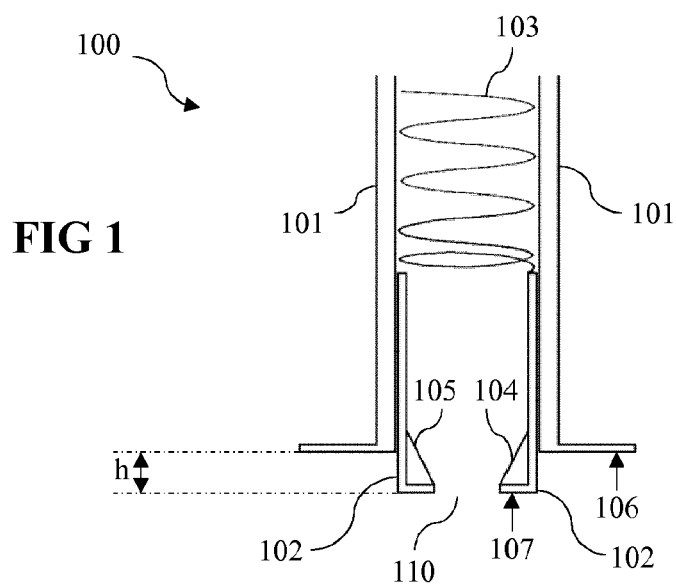
FIG. 1 illustrates a device for determining skin elasticity, according to an embodiment of the invention

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, fig., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Throughout the description reference is made to "skin dome" or "skin doming". This refers to the creation of a skin deformation which has the shape of a dome by deforming the skin physically. Thus, the skin resembling or having the shape of the upper half of a sphere under influence of a pressure.

The invention presented in this disclosure solves the problems of state of the art devices related to cost and compactness by providing a device which can be attached to e.g. the smartphone of the user. Expensive components such as the imager, the flash light and a processor are, according to an embodiment of the invention, not part of the device itself. By doing so, cost of the device is drastically reduced. In contrast to prior art devices which use pumps to create a suction pressure to deform skin, a mechanical structure which is pressed against the skin to deform the skin is presented. This further reduces cost and decreases the size of the device.

In a first aspect of the invention, a device for determining the skin elasticity is presented. The device comprises a means for attaching the device to an image recording device; a mechanical means configured for applying a pre-defined pressure to skin such that skin is deformed under the pre-defined pressure. The mechanical means is adapted such that an image of the deformed skin can be recorded by the image recording device when the device is attached to the image recording device.

Detailed embodiments of the device are described below.

FIG. 1 illustrates a cross section of an embodiment of a device 100 for determining skin elasticity. The device 100 may be attached to an image recording device 200 such as a digital camera or a smartphone. The device comprises an outer structure 101. This outer structure 101 may be a tube.

One end of the outer structure 101 may comprise an attachment means for attaching the device to the image recording device 200 (not illustrated), e.g. a smartphone. The attachment means may be a clip-on structure or a structure which allows the image recording device to slide into or attach to the device. The attachments means and the outer structure 101 are shaped such that when the device 100 is attached to the image recording device 200, the flash 202 and the imager 201 of the image recording device can be used to illuminate and take images of skin inside the outer structure 101 without being blocked by the outer structure 101.

The device 100 further comprises an inner structure 102. The inner structure 102 may be a tube. The dimensions of the inner structure 102 are selected such that the inner structure 102 fits into the outer structure 101 and such that the inner structure 102 can easily slide, e.g. move back and forth, within the outer structure 101. The end of the inner structure 102 which is located outside of the outer structure 101 features an opening 110. When the inner structure 102 is pressed against the skin, the skin protrudes through this opening 110 (see FIG. 2).

The device 100 further comprises a spring 103. The spring is located inside the outer structure 101 and is attached to the inner structure 102. The spring exerts a force on the inner structure 102. The device 100 is adapted such that when the device is not in use, e.g. not applied to skin, a part of the inner structure 102 is located outside of the outer structure 101. As illustrated in FIG. 1, when the device 100 is not pressed against skin, surface 107 of the inner structure 102 is located at a distance h from surface 106 of the outer structure 101.

Figure 2:
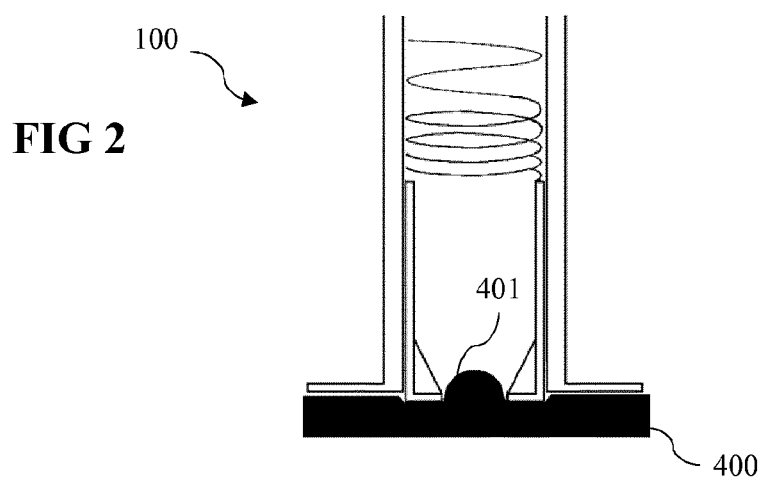
FIG. 2 illustrates a device for determining skin elasticity when applied to skin, according to an embodiment of the invention

When the device is in use, surface 107 of the inner structure 102 is pressed against the skin 400 until the inner structure 102 slides into the outer structure 101 while compressing the spring 103 until surface 106 of the outer structure 101 comes into contact with the skin. As the spring 103 is compressed, the inner structure 102 exerts a known force on the skin 400 through the spring 103. This known force is the pre-defined pressure value. This causes the area of the skin within the inner structure 102 to deform. For example, the skin forms a skin dome 401. This is illustrated in FIG. 2 which illustrates a device in use, applied on skin 400. As can be noticed, surface 107 of inner structure 102 is in contact with the skin. Via the spring 103, the inner structure 102 exerts a force on the skin which causes the skin to protrude through opening 110. When the device is fully pressed against the skin, the surface 106 of outer structure 101 is also in contact with the skin. As the force that the spring 103 is applying or exerting on the inner tube and therefore on the skin is known, skin elasticity can be determined from the image of the skin deformation, e.g. by analyzing light differences in the image. Optionally, a means for determining the distance h over which the inner tube slides into the outer tube may be present. By measuring this distance h, a more accurate determination of the force of the spring may be done leading to a more accurate determination of the skin elasticity. The means for determining the distance h may be optical, e.g. using a laser.

Figure 3:
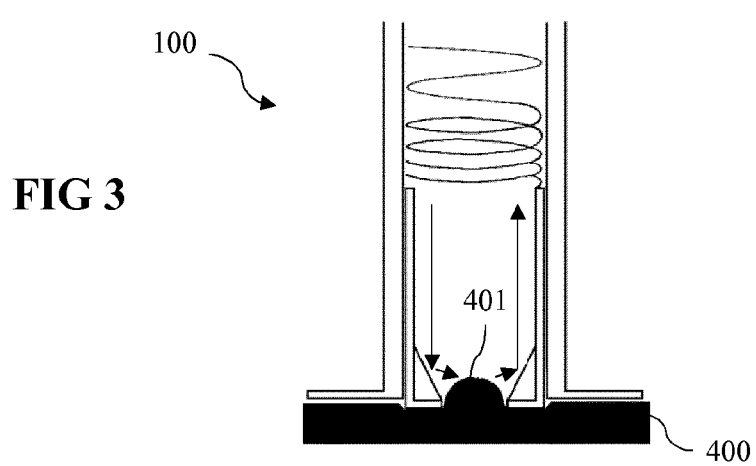
FIG. 3 illustrates the light path in a device for determining skin elasticity when applied to skin, according to an embodiment of the invention

In this embodiment, the device 100 further comprises a first and a second mirror 104, 105. The mirrors are located in the inner structure 102. The mirrors 104, 105 are positioned at an angle relative to the surface or plane of the skin when the device is applied to the skin. The mirrors 104, 105 are used to reflect light to and from the skin 400. This is illustrated in FIG. 3 with arrows. The outer structure 101 and the inner structure 102 are adapted such that flash light from the image recording device 200 reaches the skin that is deformed within the inner structure 102 and such that an image from the deformed skin 401 within the inner structure 102 can be recorded.

Figure 4:
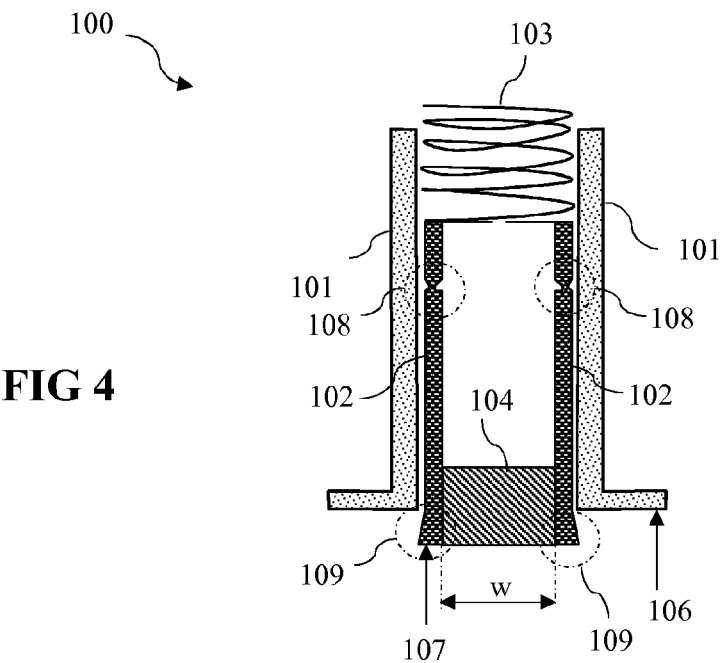
FIG. 4 illustrates a device for determining skin elasticity, according to an embodiment of the invention
Figure 5:
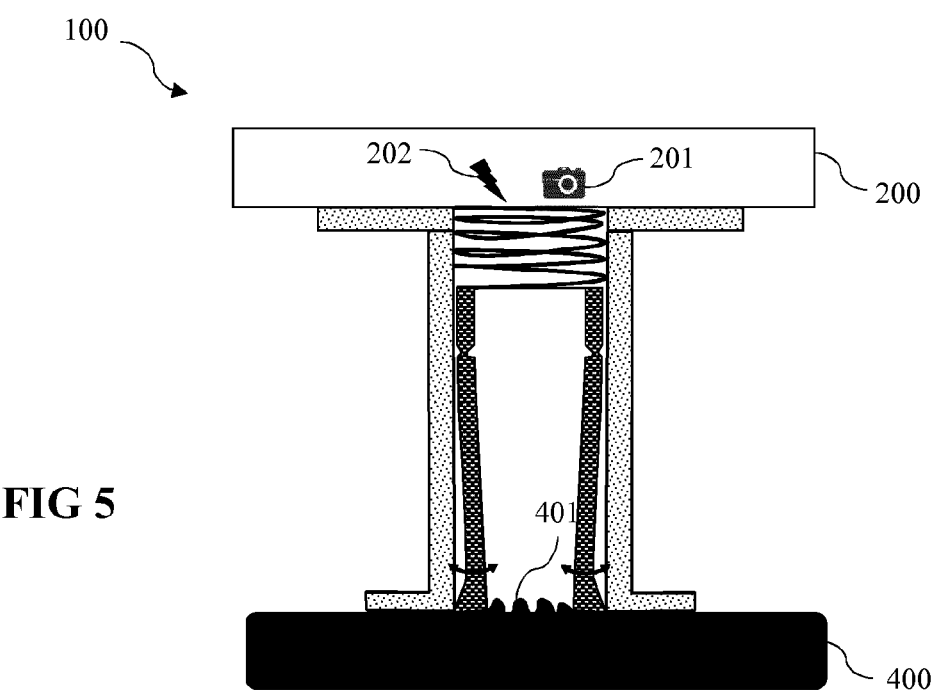
FIG. 5 illustrates a device for determining skin elasticity when applied to skin, according to an embodiment of the invention

FIG. 4 illustrates an embodiment of a device 100 for determining skin elasticity. The device is similar to the device illustrated in FIGS. 1-3. To avoid repetition, the similar device features are not described here. However, the device illustrated in FIG. 4 differs from the device illustrated in FIG. 1 in that the inner structure 102 is flexible. Further, the part of the inner structure 102 located outside of the outer structure 101 when the device is not in use features enlargements 109. For example, parts of the inner structure 102 located outside of the outer structure 101 are thicker. When the inner structure 102 and consequently the enlarged parts 109 of the inner structure 102 slide into the outer structure 101, the width w inside the inner structure 102 diminishes. The enlargements 109 of the inner structure 102 are shaped, e.g. gradually becoming larger, such that they allow the inner structure 102 to slide into the outer structure 101 without blocking the sliding movement and such that the width w within the inner structure 102 diminishes as the inner structure 102 slides into the outer structure 101. When the device is applied to skin 400, the diminishing width w of the inner structure 102 deforms the skin 400 thereby causing skin folds 401 to form. The skin folding 401 is illustrated in FIG. 5 which illustrates a device in use, applied to skin 400 and attached to an image recording device 200 comprising an imager 201 and a flash light 202. As can be noticed, surface 107 of inner structure 102 is in contact with the skin 400. Via the spring, the inner structure 102 exerts a force on the skin 400 and while the inner structure 102 slides into the outer structure 101 the skin 400 present within the inner structure 102 starts to fold within opening 110. When the device 100 is fully pressed against the skin 400, the surface 106 of outer structure 101 is also in contact with the skin 400. As the distance h over which the inner structure 102 moves and the force of the spring is known, skin elasticity can be determined from the image of the skin deformation, e.g. taking into account the amplitude or number of the formed skin folds 401.

Skin elasticity here is defined as a combination of deformation and the amount of folds for a given force and in plane compression of the skin. A higher amount of folds indicates that the skin is less able to follow compression/less flexible (older skin, degradation of collagen) while the number of the folds and the amplitude of the folds, but also the amplitude of the lowest doming frequency, in relation to the given force, defines the basic elasticity.

As the spacing within the inner structure diminishes while the inner structure slides into the outer structure, the inner structure may comprise a flexible material. For example, the inner structure comprises elastic hinges 108. Alternatively, the inner structure is fabricated from a flexible material such as a rubber. The flexibility of the inner structure is indicated in FIG. 5 with arrows.

Further, another difference with the device illustrated in FIG. 1 is that the device illustrated in FIG. 4 contains one mirror instead of two. The mirror is positioned at an angle of 45 degrees. By doing so, a viewing angle almost parallel to the skin plane is created. When an image is recorded, the resulting image is composed of a view parallel to the skin plane and a view perpendicular on the skin plane (image 3 & 4). As an advantage, the parallel view may be used for deriving the in-plane skin elasticity information, from the perpendicular image a multitude of other skin parameters can be derived.

Figure 6:
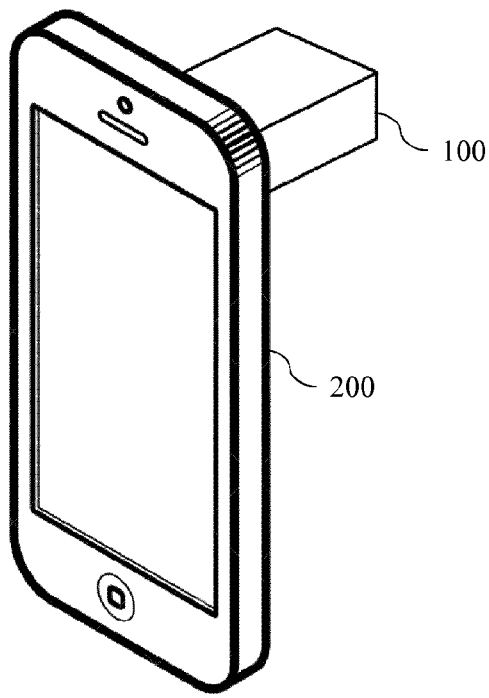
FIG. 6 illustrates a front view of a device for determining skin elasticity attached to a smartphone
Figure 7:
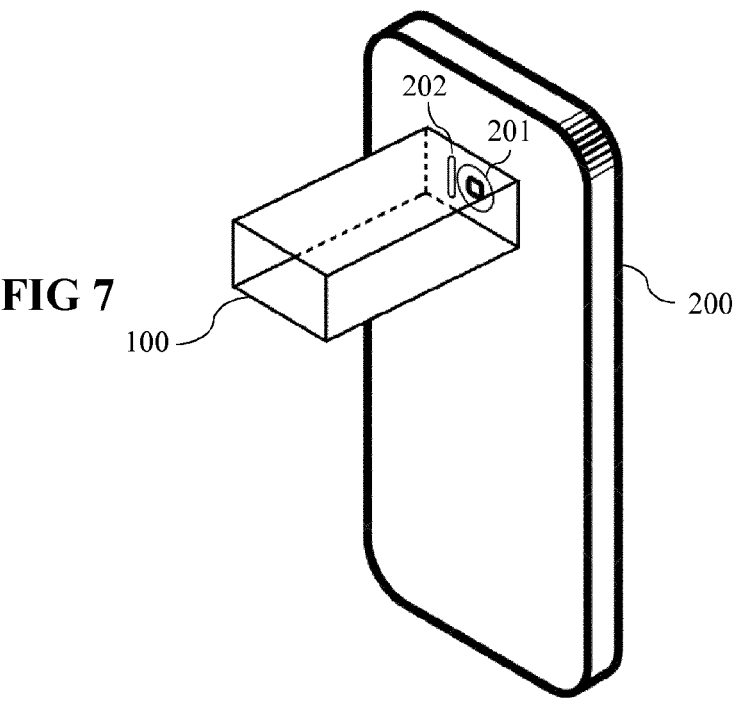
FIG. 7 illustrates a back view of a device for determining skin elasticity attached to a smartphone

FIG. 6 and FIG. 7 illustrate the attachment of the device 100 illustrated in FIGS. 1-5 to a smartphone 200. As described above, the flash light 202 and the imager 201 of the smartphone are contained within the device 100, such that skin which is deformed by the inner structure 102 of device 100 can be illuminated and recorded.

In a second aspect of the invention, a system for determining skin elasticity is presented. While the device presented in the first aspect of the invention is intended for being attached to a different device that performs image recording and image processing, the system presented in the second aspect of the invention is an integrated device that contains all components required for determining skin elasticity. The system comprises: mechanical means for exposing skin to a pre-defined pressure to create a skin deformation; an image recording device comprising an imager and a light source for imaging and illuminating the skin deformation; and a processor configured for determining an amount of deformation of the skin in the image using image processing techniques and further configured for determining skin elasticity based on the amount of skin deformation and on the pre-defined pressure value.

Figure 8:
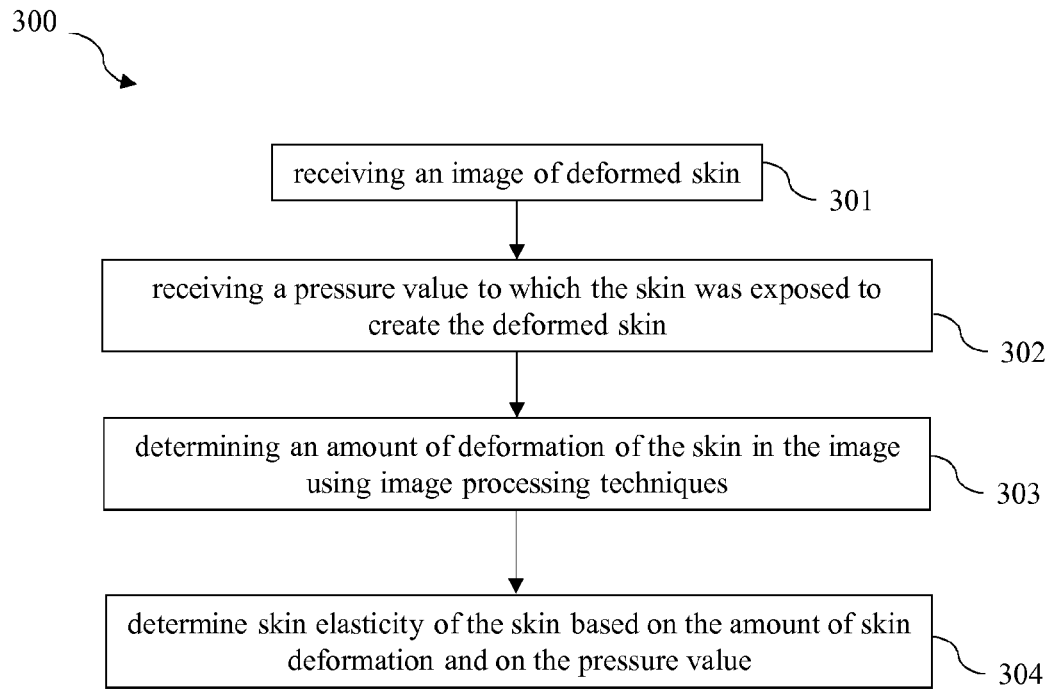
FIG. 8 is a block diagram of a method for determining skin elasticity

In a third aspect of the invention, a method 300 for determining skin elasticity of skin is presented. The method is illustrated in FIG. 8 and comprises: receiving an image of deformed skin 301; receiving a pressure value to which the skin was exposed to create the deformed skin 302; determining an amount of deformation of the skin in the image using image processing techniques 303; determining skin elasticity of the skin based on the amount of skin deformation and on the pressure value 304. The method may be a software program, for example running on a processor of an image recording device such as a smartphone. For example, the software may be an app running on the smartphone.

Alternatively, the method may comprise the following steps: applying a pressure value to skin such that the skin deforms; taking an image of the deformed skin; determine the amount of deformation of the skin in the image using image processing techniques; determine skin elasticity of the skin based on the amount of skin deformation and on the pressure value.

Depending on the deformation of the skin, different techniques may be used to determine the amount of deformation. When a skin dome is formed, for example by using one of the devices as illustrated in FIGS. 1-3, the determination of the amount of skin deformation may comprise analyzing light intensity differences in the image taken from the skin dome.

According to a particular embodiment, analyzing light intensity differences is performed by analyzing the amount of light and shadow in an image.

Example:

In a first step, the amount of pixels above and below certain thresholds for each image row, e.g. each horizontal image row, is calculated. In a second step, pixels above a defined threshold are marked white and pixels below another defined threshold are marked black. Each row now contains a number of white, black and other pixels. In third step, when the majority of the pixels in the row are white, the whole line is colored white. The number of black and white lines is transformed into a "roundness" value that represents the skin elasticity.

Figure 9:
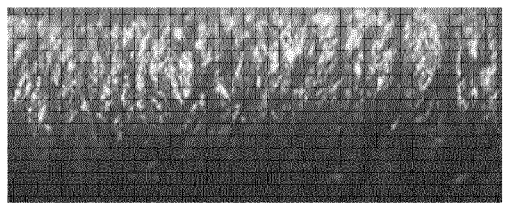
FIG. 9 is an image of deformed skin
Figure 10:
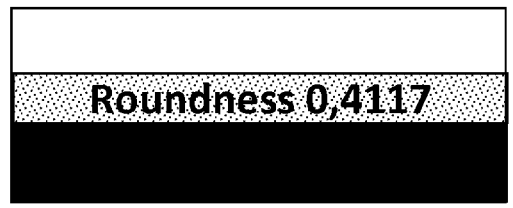
FIG. 10 is a representation of the output of an algorithm for determining skin elasticity of the skin presented in FIG. 9
Figure 11:
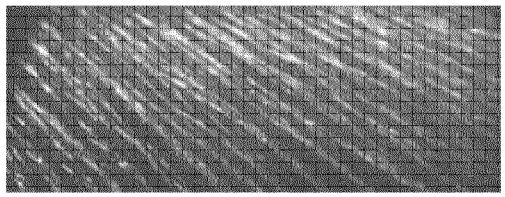
FIG. 11 is an image of deformed skin
Figure 12:
FIG. 12 is a representation of the output of an algorithm for determining skin elasticity of the skin presented in FIG. 11

FIG. 9 is an image of skin that is exposed to a pressure causing the skin to dome. FIG. 10 illustrates the result after analysis of the amount of light and shadow in the image as described above. FIG. 11 is another image of skin that is exposed to another pressure causing the skin to dome. FIG. 12 illustrates the result after analysis of the amount of light and shadow in the image as described above.

When under pressure skin folds are formed, for example by using one of the devices as illustrated in FIGS. 4-5, the determination of the amount of skin deformation comprises determining amplitude and/or determining an amount of skin folds in the deformed skin area.

According to a particular embodiment, determining the amount of skin folds in the deformed skin area is performed by performing edge detection on an image of the deformed skin and analyzing the detected edges. The determination of the amplitude may be performed e.g. by analysis of the gradient of change in RGB values of adherent pixels.

The invention claimed is:

1. A device for measuring elasticity of skin, the device comprising:

an outer structure having a first end and a second end opposite the first end;

means for attaching the outer structure to an image recording device at the first end, wherein the attached image recording device comprises an imager and a light source, wherein the light source emits light from the first end of the outer structure to which the image recording device is attached;

an inner structure partly located inside the outer structure, wherein a part of the inner structure is located outside of the outer structure at the second end, and wherein the inner structure is moveable inside the outer structure;

a spring for providing a pre-defined pressure when the device is pressed against the skin, wherein the spring is coupled to the inner structure and positioned such that it compresses when the part of the inner structure moves inside the outer structure, wherein the inner structure is configured to cause the skin to deform when the device is pressed against the skin and the inner structure moves inside the outer structure, and wherein an end of the inner structure that touches the skin defines an opening through which at least one protruding portion of the skin protrudes into the inner structure when the device is pressed against the skin; and a first mirror positioned inside the inner structure, wherein the first mirror is configured to direct light, emitted by the light source of the attached image recording device at the first end of the outer structure, toward the at least one protruding portion of the skin, enabling the imager to acquire an image of the at least one protruding portion of the skin through the outer structure.

2. The device according to claim 1, wherein the first mirror is positioned such that the image acquired by the imager contains a view of the at least one protruding portion of the skin under an angle.

3. The device according to claim 2, wherein the device further comprises a second mirror, wherein the first mirror is positioned for reflecting light towards the at least one protruding portion of the skin from one direction, and wherein the second mirror is positioned for reflecting light towards the at least one protruding portion of the skin from another direction.

4. The device according to claim 1, wherein the inner structure comprises two elements configured to move towards each other when the device is pressed against the skin and the inner structure moves inside the outer structure thereby causing the skin in between the two elements to fold, providing the at least one protruding portion of the skin.

5. The device according to claim 1, wherein the inner structure comprises two elements configured to cause doming of skin present between the two elements, providing the at least one protruding portion of the skin, when the device is pressed against the skin and the inner structure moves inside the outer structure.

6. A system for determining skin elasticity, comprising:
the device according to claim 1; and
a processor configured for determining an amount of deformation of the skin in the image of the at least one protruding portion of the skin using image processing techniques, and for determining skin elasticity based on the determined amount of skin deformation and on the pre-defined pressure.

7. The system according to claim 6, wherein determining the amount of deformation of the skin comprises determining amplitude and/or determining an amount of skin folds in the at least one protruding portion of the skin.

8. The system according to claim 6, wherein determining the amount of deformation of the skin comprises analyzing light intensity differences in the image.

9. The device according to claim 1, wherein the attached image recording device comprises a smartphone.

10. The device according to claim 1, wherein the inner structure is flexible, and comprises enlargements at the end of the inner structure that touches the skin, wherein the enlargements are shaped to enable the inner structure to slide into the outer structure without being blocked, and to cause a width within the inner structure to diminish as the inner structure slides into the outer structure.

11. The device according to claim 10, wherein the flexible inner structure comprises elastic hinges, enabling the width within the inner structure to diminish as the inner structure slides into the outer structure.

12. The device according to claim 10, wherein the flexible inner structure is fabricated from a flexible material, enabling the width within the inner structure to diminish as the inner structure slides into the outer structure.

13. A method for determining skin elasticity of skin with a device comprising an outer structure having a first end and a second end opposite the first end; an inner structure partly located inside the outer structure, wherein a part of the inner structure is located outside of the outer structure at the second end, and wherein the inner structure is moveable inside the outer structure; and a spring providing a pre-defined pressure when the device is pressed against the skin, wherein the spring is coupled to the inner structure and positioned such that it compresses when the part of the inner structure moves inside the outer structure, the method comprising:
attaching an image recording device to the first end of the outer structure via an attachment mechanism, the attached image recording device comprising an imager and a light source;
pressing the device against the skin, causing the inner structure to move inside the outer structure, and at least one protruding portion of the skin to protrude into the inner structure through an opening defined at an end of the inner structure that touches the skin;
redirecting light, emitted from the light source of the attached image recording device at the first end of the outer structure, toward the at least one protruding portion of the skin via at least one mirror positioned inside the inner structure;
receiving an image of the at least one protruding portion of the skin through the outer structure at the imager;
receiving image data of the image at a processor;
receiving a pressure value to which the skin was exposed to create the at least one protruding portion of the skin at the processor;
determining an amount of deformation of the skin in the image using image processing techniques at the processor; and
determining skin elasticity of the skin based on the amount of deformation of the skin and on the pressure value at the processor.

14. The method according to claim 13, wherein determining the amount of deformation of the skin comprises determining amplitude and/or determining an amount of skin folds in the at least one protruding portion of the skin.

15. The method according to claim 13, wherein determining the amount of the skin deformation comprises analyzing light intensity differences in the image at the processor.

16. The method according to claim 15, wherein analyzing the light intensity differences comprises:
setting a light intensity threshold;
calculating an area of the image having a light intensity larger than the threshold; and
determining the amount of deformation of the skin based on the calculated area.

17. The method according to claim 15, wherein analyzing light intensity differences comprises:
setting a first light intensity threshold;
calculating a first area of the image having a light intensity higher than the first light intensity threshold;
setting a second light intensity threshold being lower than the first light intensity threshold;
calculating a second area of the image having a light intensity lower than the second light intensity threshold; and
determining the amount of deformation of the skin using the calculated first and second area.

18. The method according to claim 15, wherein the attached image recording device comprises a smartphone.

19. A device for measuring elasticity of skin, the device comprising:
an outer structure having a first end and a second end opposite the first end;
means for attaching the outer structure to an image recording device at the first end, wherein the image recording device comprises an imager and a light source;
an inner structure partly located inside the outer structure, wherein a part of the inner structure is located outside of the outer structure at the second end, and wherein the inner structure is moveable inside the outer structure, wherein the inner structure is configured to cause the skin to deform when the device is pressed against the skin and the inner structure moves inside the outer structure, and wherein an end of the inner structure that touches the skin defines an opening through which at least one protruding portion of the skin protrudes into the inner structure when the device is pressed against the skin; and a spring for providing a pre-defined pressure when the device is pressed against the skin, wherein the spring is coupled to the inner structure and positioned such that it compresses when the part of the inner structure moves inside the outer structure; and a first mirror positioned inside the inner structure, wherein the first mirror is configured to direct light from the light source, passing through the outer structure from the first end to the second end, toward the at least one protruding portion of the skin, enabling the imager to acquire an image of the at least one protruding portion of the skin through the outer structure, wherein the spring is arranged circumferentially inside the outer structure such that the light from the light source, passing through the outer structure from the first end to the second end, passes through the spring.

\* \* \* \* \*